(12) United States Patent
Covey et al.

(10) Patent No.: US 6,440,687 B1
(45) Date of Patent: Aug. 27, 2002

(54) METHOD OF PROTEIN ANALYSIS

(75) Inventors: Thomas R. Covey; Eric Huang; Jack Henion, all of Ithaca, NY (US)

(73) Assignee: MDS Sciex, Concord (CA)

( * ) Notice: Subject to any disclaimer, the term of this patent is extended or adjusted under 35 U.S.C. 154(b) by 0 days.

(21) Appl. No.: 09/357,476

(22) Filed: Jul. 20, 1999

Related U.S. Application Data (63) Continuation of application No. 07/994,477, filed on Dec. 21, 1992, now Pat. No. 5,952,653, which is a continuation of application No. 07/354,617, filed on May 19, 1989, now abandoned.

(51) Int. Cl.$^7$ .............. C12Q 1/37; C12N 1/00; C12M 1/36; B01D 59/44
(52) U.S. Cl. ............ 435/23; 250/288; 435/317.1; 435/287.3; 435/288.2; 435/288.6
(58) Field of Search ............... 435/23, 317.1, 435/287.3, 287.6, 288.2, 288.6; 250/288

(56) References Cited

U.S. PATENT DOCUMENTS 4,861,988 A 8/1989 Henion et al.
4,885,076 A * 12/1989 Smith et al.

OTHER PUBLICATIONS

Johnson et al. (Mar. 10, 1987) The primary structure of thioredoxin from chromatium vinosum determined by high-performance tandem mass spectrometry, Biochemistry vol. 26, No. 5, pp. 1209–1214.*
Kenndler et al. (1981) Off–line combination of isotachophoresis and mass spectrometry, J. Chromatogr. vol. 209, No. 2, pp. 306–309, abstract only.*
Dietrich et al. (1981) Primary structure of the southern bean mosaic virus coat protein, Archives of Biochemistry and Biophysics vol. 210, No. 2, pp. 794–796.*
Mock et al., (1989) Application of on–line HPLC–FAB mass spectrometry to the analysis of enzymatic digests of ribonuclease B. Organic Mass Spectrometry, vol. 24, pp. 591–596.*
Biemann, K.; Nov. 1986; Mass Spectrometoic Methods for Protein Sequencing Analytical Chemistry 58:1288–1300.
Biemann, K.; 1988; Contribution of Mass Spectrometry to Peptide and Protein Structure. Biomedical and Environmental Mass Spectrometry, 16:99–111.
Biemann et al., 1987; Science, 237, p.992–998.
Bruins et al., 1987, Anal. Chem., 59, pp. 2642–2626.
Busch et al., 1982, Science, 218, pp. 247–254.

(List continued on next page.)

*Primary Examiner*—Jon P. Weber
(74) *Attorney, Agent, or Firm*—Ropes & Gray; Matthew P. Vincent; Yu Lu (57) ABSTRACT

A method of analyzing a protein, namely determining the amino acid sequence of a protein is described. Trypsin is added to a protein to form a liquid phase mixture of trypsin and the protein. The disulfide linkages of the protein may be reduced and the resulting sulfhydryl groups alkylated either before or after the addition of trypsin. The trypsin is allowed to digest the protein long enough to cleave protein into tryptic fragments. A portion of the digested mixture is ionized by ion evaporation to produce gas phase ions of the tryptic fragments, the gas phase ions being predominantly doubly charged with one charge at each end of the doubly charged ions. The gas phase ions of the tryptic fragments are analyzed by sequentially selecting therefrom ions of a desired mass to charge ratio in a first mass analyzer. The selected ions are fragmented by collision in a second mass analyzer to produce daughter ions, and the daughter ions are then analyzed in a third mass analyzer.

27 Claims, 10 Drawing Sheets

OTHER PUBLICATIONS

Carr, S.A. et al.; 1988; Mass Spectrometry in Biopharmaceutical Research in Macromolecular Sequencing and Tynthesis: Selected Methods and Applications, pp. 83–99, [ed] A.R. Liss, Inc.

Cody et al., 1985, Proc. Nat'l Acad. Sci. U.S.A., 82, p. 6367–6370.

Cooks et al., Mar. 25, 1991, Chem. Eng. News, pp. 26–41.

Covey, T.R., et al., 1988, The Determination of Protein, Oligonucleotide and Peptide Molecular Weights by Ion–Spray Mass Spectrometry, Rapid Communications in Mass Spectrometry, 2: 240–256.

Fenn et al., 1989, Science, 246: 64–71.

Hunkapiller et al., 1984, Science, 226: 304–311.

Hunt, D.F. et al., 1989, Oligopeptide Sequence Analysis by Collision–activated Dissociation of Multiply Charged Ions in Rapid Communications in Mass Spectrometry, vol. 3, No. 4, p. 122.

Olivares et al., 1987, Anal. Chem., 59, 1230–1232.

Stryer, 1988, "Biochemistry, Third Edition", p. 56.

Vestal, 1984, Science, 226, 275–281.

Yost et al., 1979, Anal. Chem., 51, 1251A–1264A.

* cited by examiner

FIG.8

METHOD OF PROTEIN ANALYSIS

This application is a Continuation of application Ser. No. 07/994,477, filed Dec. 21, 1992, now U.S. Pat. No. 5,952,653, which a File Wrapper Continuation of application Ser. No. 07/354,617, filed May 19, 1989, now abandoned, which application(s) are incorporated herein by reference.

FIELD OF THE INVENTION

This invention relates to a method of protein analysis. More particularly it relates to a method of analyzing proteins to obtain information which can be used to determine the structure of the protein, namely sequence of the amino acids making up the protein.

BACKGROUND OF THE INVENTION

In the past, protein sequencing has been carried out by techniques such as those involving the sequential removal of amino acids from one end of the protein and identifying each removed amino acid in turn. Other techniques have relied on the genetic code, using the base sequence of the gene coding for the protein. Both these techniques are slow, complex and difficult.

More recent techniques have attempted to obtain amino acid sequence information using mass spectrometry, typically using fast atom bombardment to ionize the sample. In fast atom bombardment, a sample dissolved in a liquid is bombarded with atoms or ions. Charged molecules resulting from this process are directed into the mass spectrometer and detected. An example of this technique is described in the text entitled "Macro Molecular Sequencing and Synthesis Selected Methods and Applications", 1988, published by Alan R. Liss, Inc., specifically at pages 83 to 99 in an article in such text entitled "Mass Spectrometry in Bio-Pharmaceutical Research" by Steven A. Carr et al.

A difficulty with the technique using mass spectrometry is that when complex protein molecules are fragmented, analysis of the daughter or fragment ions has been extremely difficult. As noted by Carr et al at page 86 of the above identified text, a Y-B analysis technique can be used to determine sequence information. However the analysis is complex, slow and difficult, and so far as the applicant is aware has never been commercially used.

According to the invention an improved method of analyzing proteins is provided, utilizing ion evaporation followed by tandem mass spectrometry. The method of the invention provides tryptic fragments which are predominantly doubly charged, one charge being located at each end of the fragment. Such fragments are then further fragmented into two singly charged daughter fragments or daughter ions in the tandem mass spectrometer, providing information which can be much more readily used to obtain the sequence of the amino acids in the protein.

BRIEF SUMMARY OF THE INVENTION

In its broadest aspect the invention provides a method of analyzing a protein comprising the steps of:

(1) adding trypsin to said protein to form a liquid phase mixture of trypsin and said protein, (2) optionally reducing the disulfide linkages and alkylating the resulting sulfhydryl groups of said protein either before or after said step (1), (3) allowing the trypsin to digest said protein long enough to cleave said protein into tryptic fragments in said liquid phase, (4) ionizing a portion of the digested mixture by ion evaporation to produce gas phase ions of said tryptic fragments from said liquid phase, said gas phase ions being predominantly doubly charged with one charge at each end of said doubly charged ions, (5) and analyzing said gas phase ions of said tryptic fragments by sequentially selecting therefrom ions of a desired mass to charge ratio in a first mass analyzer, fragmenting such selected ions by collision in a second mass analyzer to produce daughter ions, and then analyzing said daughter ions in a third mass analyzer.

Further objects and advantages of the invention will appear from the following description, taken together with the accompanying drawings.

DETAILED DESCRIPTION OF PREFERRED EMBODIMENT

According to the invention, the protein to be analyzed is first treated with the enzyme trypsin to reduce it to tryptic fragments. The molecular weight of each fragment is generally less than about 4000 daltons, typically about 3000 daltons. As is well known, trypsin specifically cleaves proteins into fragments at the carboxyl terminus of arginine and lysine.

If the protein contains more than one covalently cross-linked polypeptide chain, the disulfide linkages of the protein can be reduced, and the resulting sulfhydryl groups alkylated, either before or after the digestion with trypsin. Mercaptoethanol can be used to reduce the sulfide linkages to sulfhydryl groups and iodoacetate can be used to alkylate the sulfhydryl groups.

The digestion of the protein with trypsin can be carried out using known methods. The mixture of the protein with trypsin, all in a liquid phase, is typically left for several hours or overnight, to allow the cleavage reaction to be completed. The resultant fragments are referred to as tryptic fragments.

Figure 2:
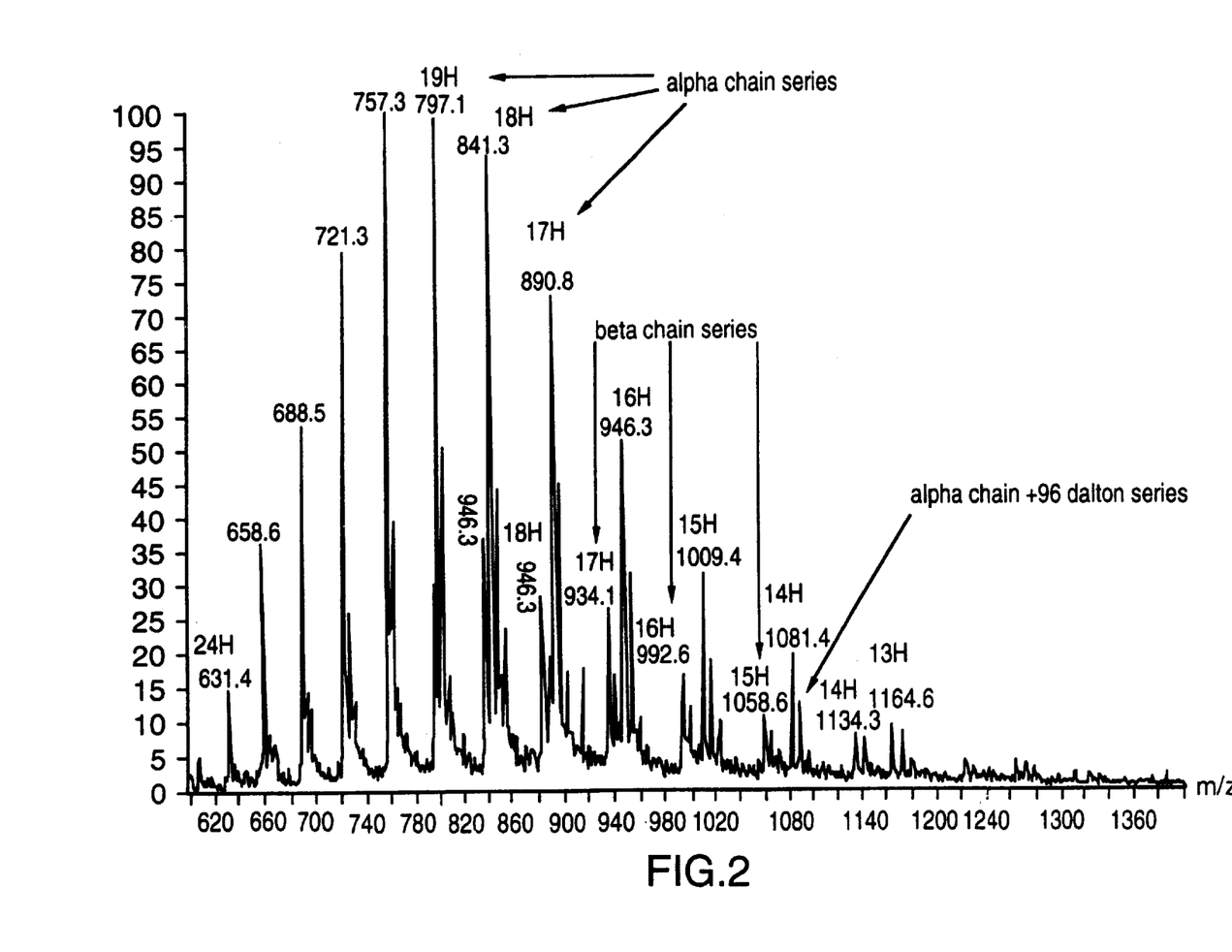
FIG. 2 is a chart showing a typical mass spectrum for human hemoglobin, with mass to charge ratio plotted on the horizontal axis and ion counts on the vertical axis.
Figure 6:
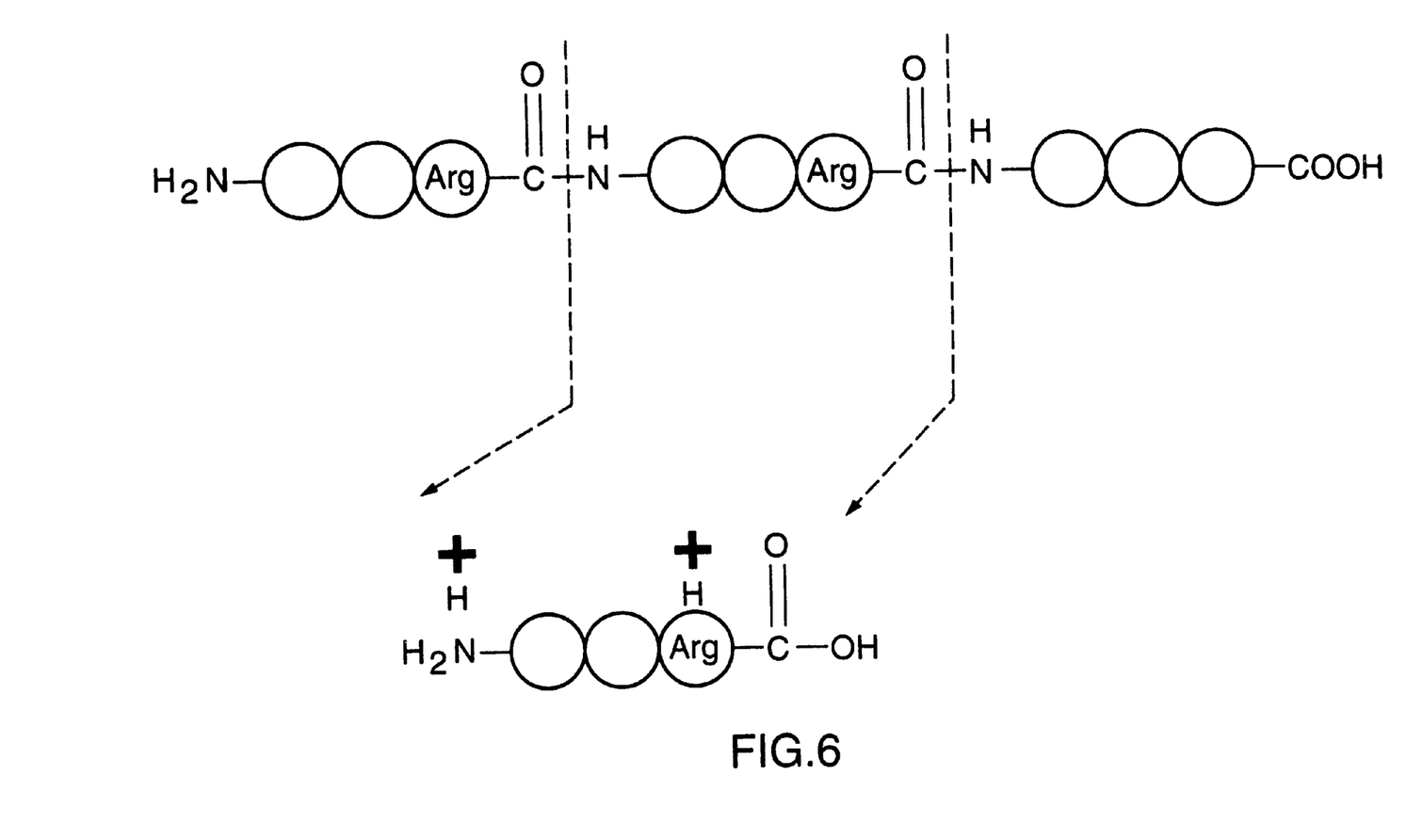
FIG. 6 is a diagrammatic view showing a typical tryptic fragment and showing why such fragments yield doubly charged ions.

Arginine and lysine are both very basic and each pick up a positively charged proton in solution. Thus, the tryptic fragments will be doubly charged because of the inclusion of arginine or lysine and an amino terminus in each fragment. (There are three exceptions to this, which will be discussed presently.) This is shown in FIG. 6, where a portion of a complete protein molecule is shown at 2. The empty circles in the protein molecule represent amino acids. FIG. 2 also shows at 4 a tryptic fragment which has been cleaved from the molecule 2. The fragment 4 has a proton or positive charge at each end thereof.

Separation procedures based on size (e.g. gelfiltration), solubility (e.g. isoelectric precipitation), electric charge (e.g. electrophoresis, isoelectric focusing, ion exchange chromatography) or ligand specificity (e.g. affinity chromatography) may be used to separate the mixture of tryptic fragments. Preferred separation procedures are high performance liquid chroinatography (HPLC), capillary zone electrophoresis or isotacho electrophoresis, most preferably HPLC. A liquid chromatograph 6 is shown as the separating instrument in FIG. 1. When a liquid chromatograph is used, the separation is a result of different components of a mixture having a different chemical affinity for the column and mobile phase, i.e. different components elute from the column at different times.

Figure 1:
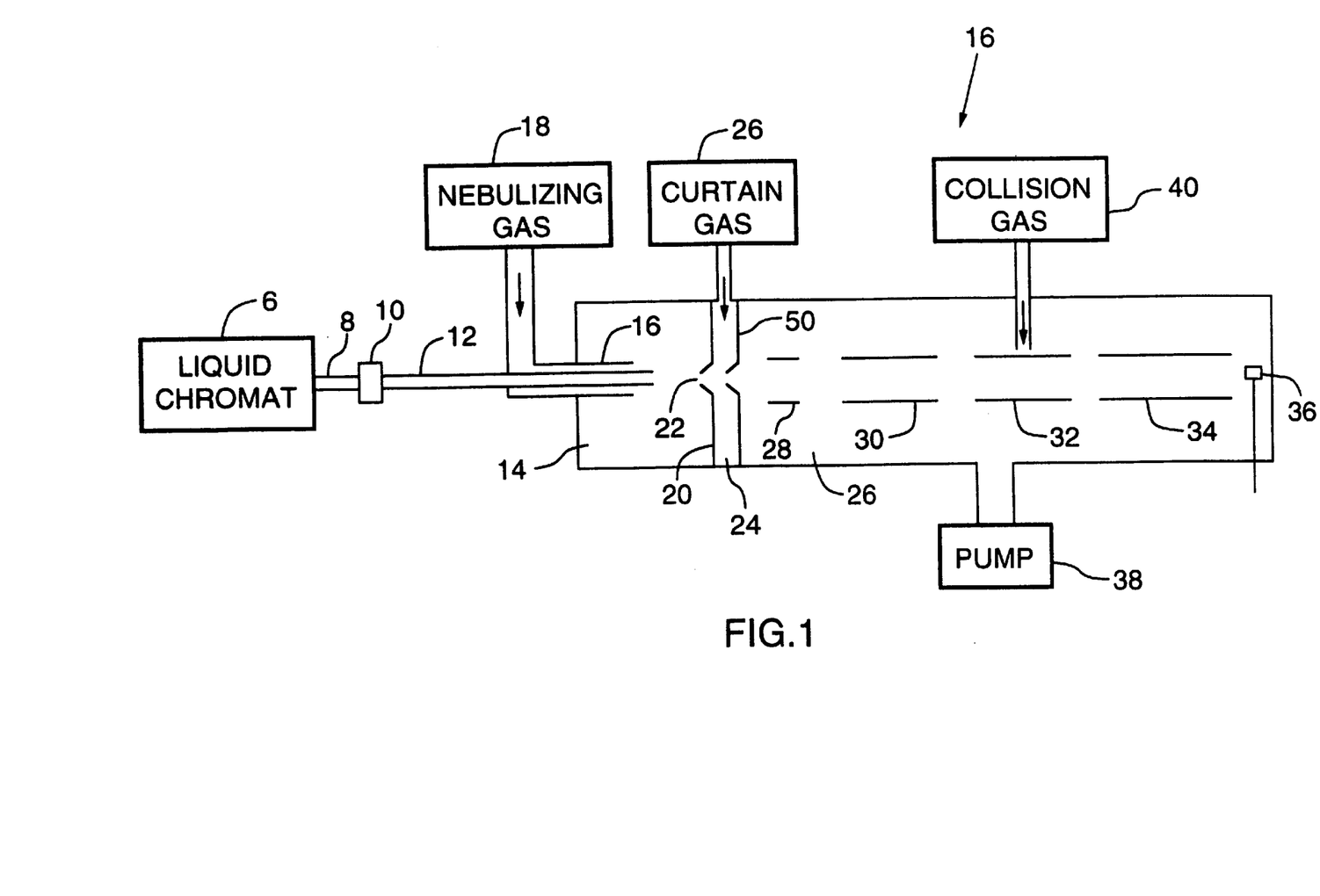
FIG. 1 is a diagrammatic view of an instrument for carrying out the method of the invention.

The separated mixture of components is next directed through a capillary 8, coupler 10 and further capillary 12 into the ionizing chamber 14 of a mass spectrometer generally indicated at 16. Mass spectrometer 16 is typically a model API III MS—MS sold by the Sciex Division of MDS Health Group Limited of Thornhill, Ontario, Canada.

It is an important feature of the invention that the ionization of the liquid mixture which occurs in ionizing chamber 14 be by a process known as ion evaporation. In ion evaporation, the liquid to be ionized is dispersed into a large number of very small charged droplets. As the droplets evaporate and become smaller, the field strength in each droplet becomes sufficiently high that ions in the droplet are ejected intact from the droplet. The inventor has determined that the locations of the charges on the gas phase ions produced by ion evaporation are at the same positions in the tryptic fragments as they are in the liquid solution phase, i.e. on the arginines and lysines. The surprising result is that virtually every tryptic fragment (with the exceptions discussed below) will be doubly charged, and the charges will be located one at each end of each fragment.

Ion evaporation can be carried out by the ion spray process described in co-pending U.S. application Ser. No. 07/103,056 filed Sep. 30, 1987 entitled "ION SPRAY APPARATUS AND METHOD" of J. D. Henion et al. axial with an outer conduit 16 through which a nebulizing gas (e.g. nitrogen) from a source 18 is directed at a velocity of at least 50 meters per second, and preferably much faster (e.g. 144 meters per second). An electric field of e.g. 3 kilovolts is applied to the tip of tube 12, while orifice plate 20 at the downstream end of ionizing chamber 14 is grounded. The combination of the nebulizing gas and the electric field produces ion evaporation in which the gas phase ions are doubly charged (with one charge at each end thereof) as discussed.

The resultant ions are directed through an orifice 22 in plate 20, and through a curtain gas chamber 24. Curtain gas chamber 24 is supplied from source 26 with an inert curtain gas which effuses through orifice 22 into chamber 14 as described in U.S. Pat. No. 4,137,750 issued Feb. 6, 1979. This prevents everything except ions from entering vacuum chamber 26 of the mass spectrometer.

The ions entering the vacuum chamber 26 are focussed by focussing lenses diagrammatically indicated at 28 through a first quadrupole mass spectrometer 30, a second quadrupole mass spectrometer 32, and a third quadrupole mass spectrometer 34 (all in tandem). A detector 36 at the downstream end of mass spectrometer 34 indicates the ion counts received. Vacuum chamber 26 is evacuated by a pump 38, and collision gas when required (as will be explained) is provided by a source 40.

Figure 3:
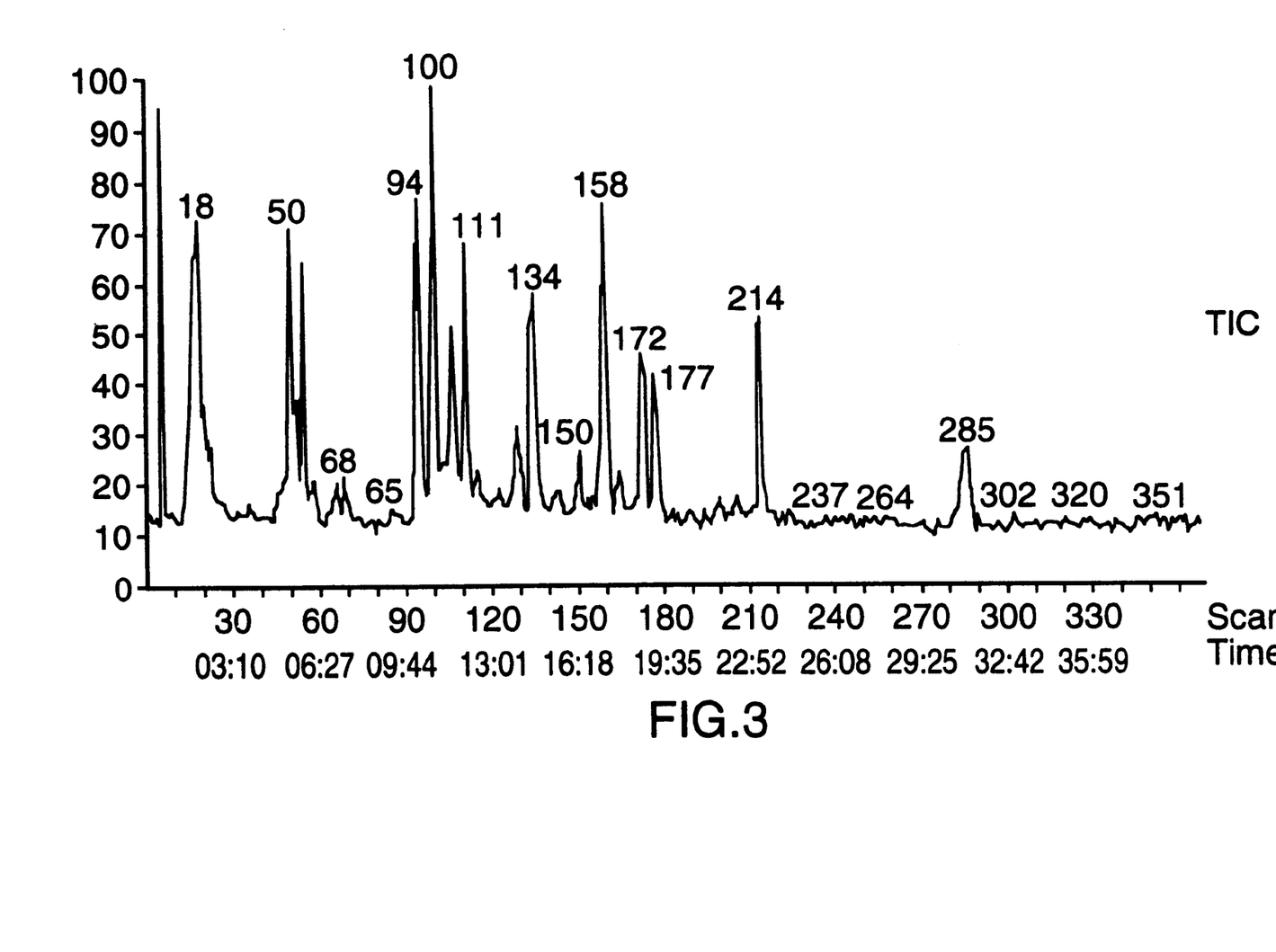
FIG. 3 is a chart showing a scan of a tryptic digest of human hemoglobin showing scan time on the horizontal axis and total ion count on the vertical axis.

In the first stage of analysis, the liquid tryptic fragment sample passing through the liquid chromatograph 6 (or other component separating instrument) is ionized by ion evaporation as shown and then directed into the vacuum chamber 26. One only of the mass spectrometers 30, 32, 34 is operated selectively (typically the first mass spectrometer 30 is operated selectively) to scan the various masses as the column eluant is ionized and as the ions are directed into the vacuum chamber. The resultant scan for a tryptic digest of human hemoglobin is shown in FIG. 3. The scanning time is approximately 40 minutes. Several scan numbers (specifically 94, 100, 111, 158, 177) are shown marked in FIG. 3 to indicate typical peaks of interest at the times when those scans occurred.

The purpose of the scan shown in FIG. 3 is to determine what masses are present. In addition of course, the time at which each mass elutes provides some information about the protein being analyzed. However it will be realized that each scan is actually a scan of a complete mass spectrum at the time of the scan, and the contents of each scan (i.e. each mass spectrum) are stored in the computer memory of the instrument as data.

Figure 4A:
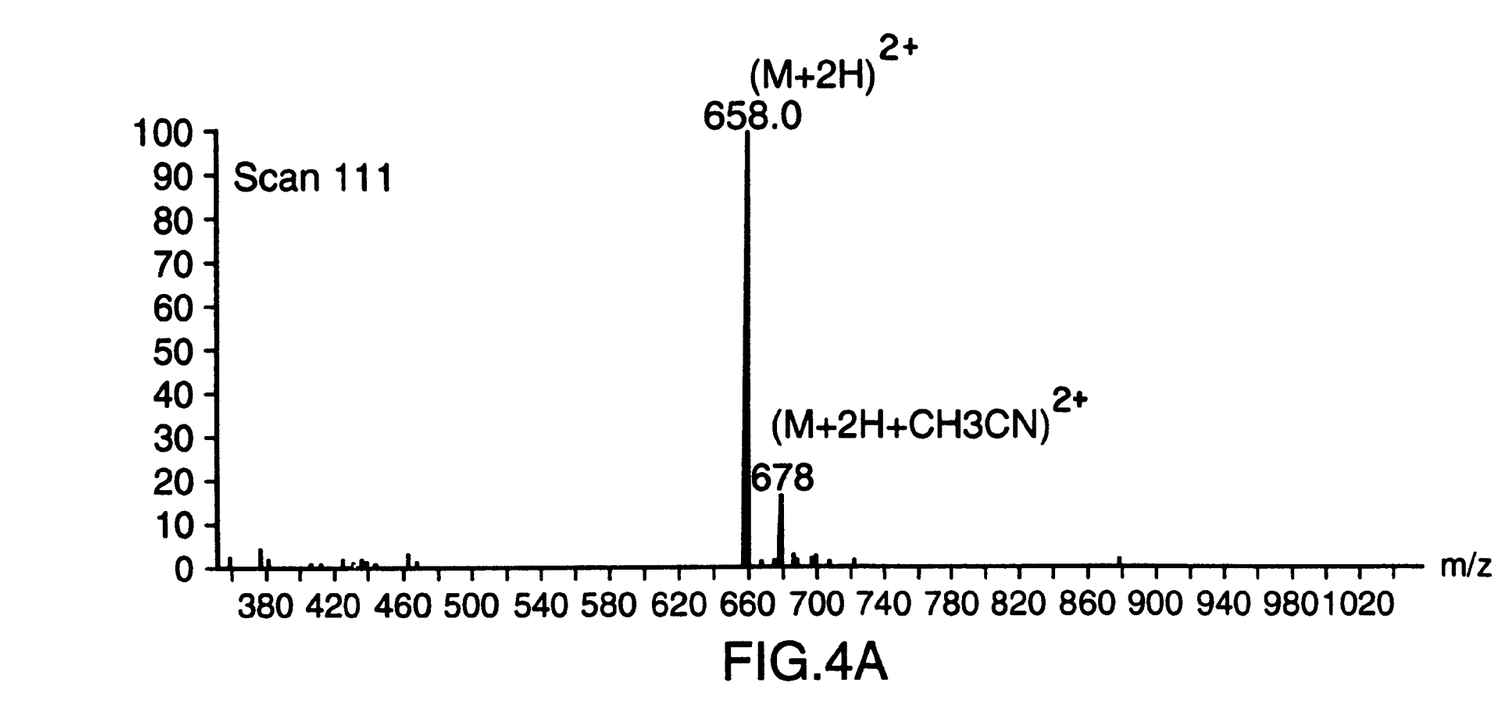
FIGS. 4A, 4B and 4C show mass spectra for scans 111, 158 and 177 respectively from FIG. 3.
Figure 4B:
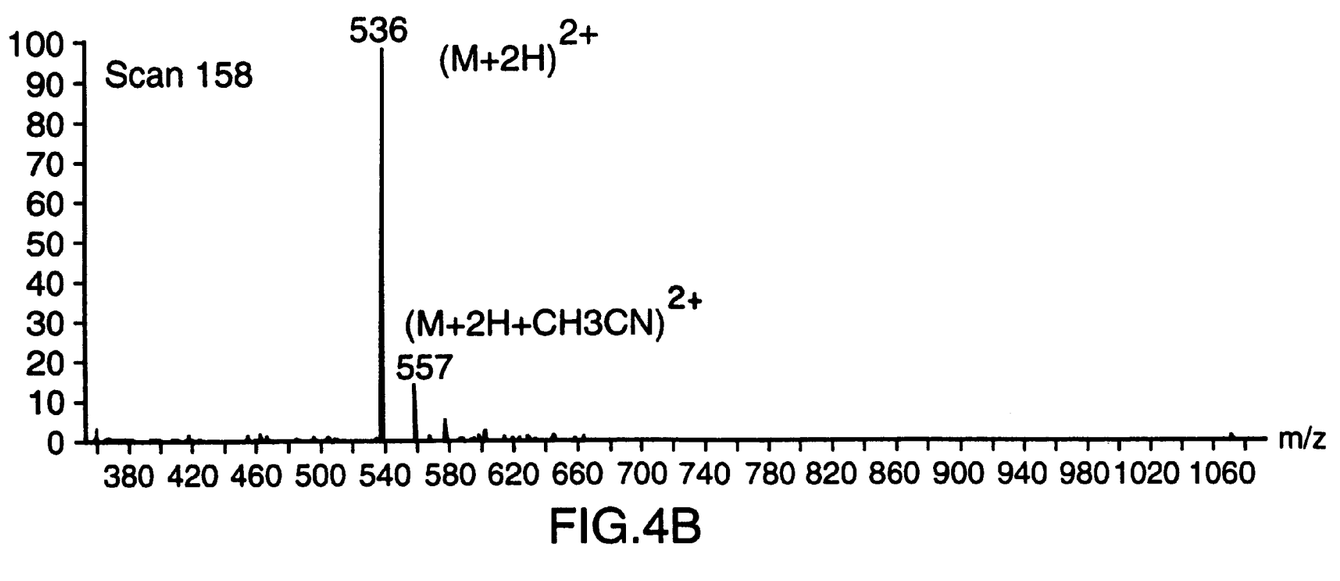
Figure 4C:
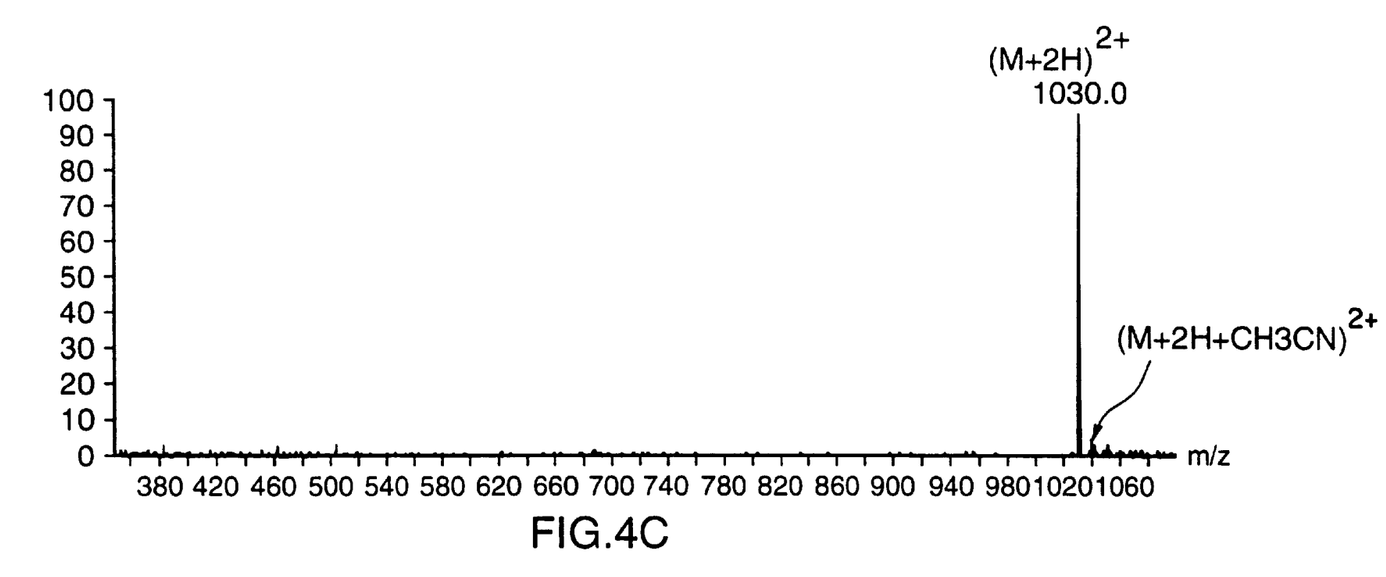

FIGS. 4A, 4B and 4C show representative mass spectra obtained from scans 111, 158 and 177 respectively. Consider FIG. 4A. This drawing shows a peak at mass to charge ratio 658. It is apparent that this peak represents a doubly charged fragment, since there is an adjacent smaller peak at mass to charge ratio 678. The difference between the two peaks in FIG. 4A is caused by some of the solvent, namely acetonitrile, adhering to the fragment. Since acetonitrile has a molecular weight of 41, and since the separation between the two peaks is about 20, it is evident that the fragment was doubly charged. The same observation can be made in FIGS. 4B and 4C.

In FIG. 4A the peak at mass to charge ratio 658 represents a molecule M having a mass 1314. This is because twice 658 is 1316, but subtracting the mass of two protons (the two positive charges) gives a resultant mass of 1314.

The individual mass spectra of the fragments of interest thus gives the molecular weight of these fragments. The next stage is to determine the structure of the fragments, i.e. the amino acid sequence in the fragments.

For this purpose, a second stage of analysis is performed. In this second stage, a motor driven hypodermic syringe (not shown), containing a further portion of the same liquid tryptic fragment mixture as used in the first stage, injects its contents directly into the capillary 12 and hence into the ionizing chamber 14. At this time, all three quadrupole mass spectrometers 30, 32 and 34 are used in the well known MS-CID-MS mode for analysis. Specifically, quadrupole 30 is scanned to select sequentially ions of interest which are permitted to pass through quadrupole 30 to quadrupole 32. At quadrupole 32, a collision gas is released from source 40 to cause collision induced dissociation of the tryptic fragments, producing daughter tryptic fragment ions. The daughter ions are scanned by quadrupole mass spectrometer 34 and detected by detector 36.

It will be appreciated that since the tryptic fragment ions leaving mass spectrometer 30 are essentially all doubly charged ions with the charges localized one at each end, therefore essentially all daughter ions will be singly charged. This is precisely the situation desired, because otherwise it can be very difficult to determine the number of charges on daughter ions and thus their actual masses would be ambiguous. Further, there are no longer neutral losses, since essentially no neutrals are produced by the process (and of course only fragments having a charge can be detected).

Figure 7:
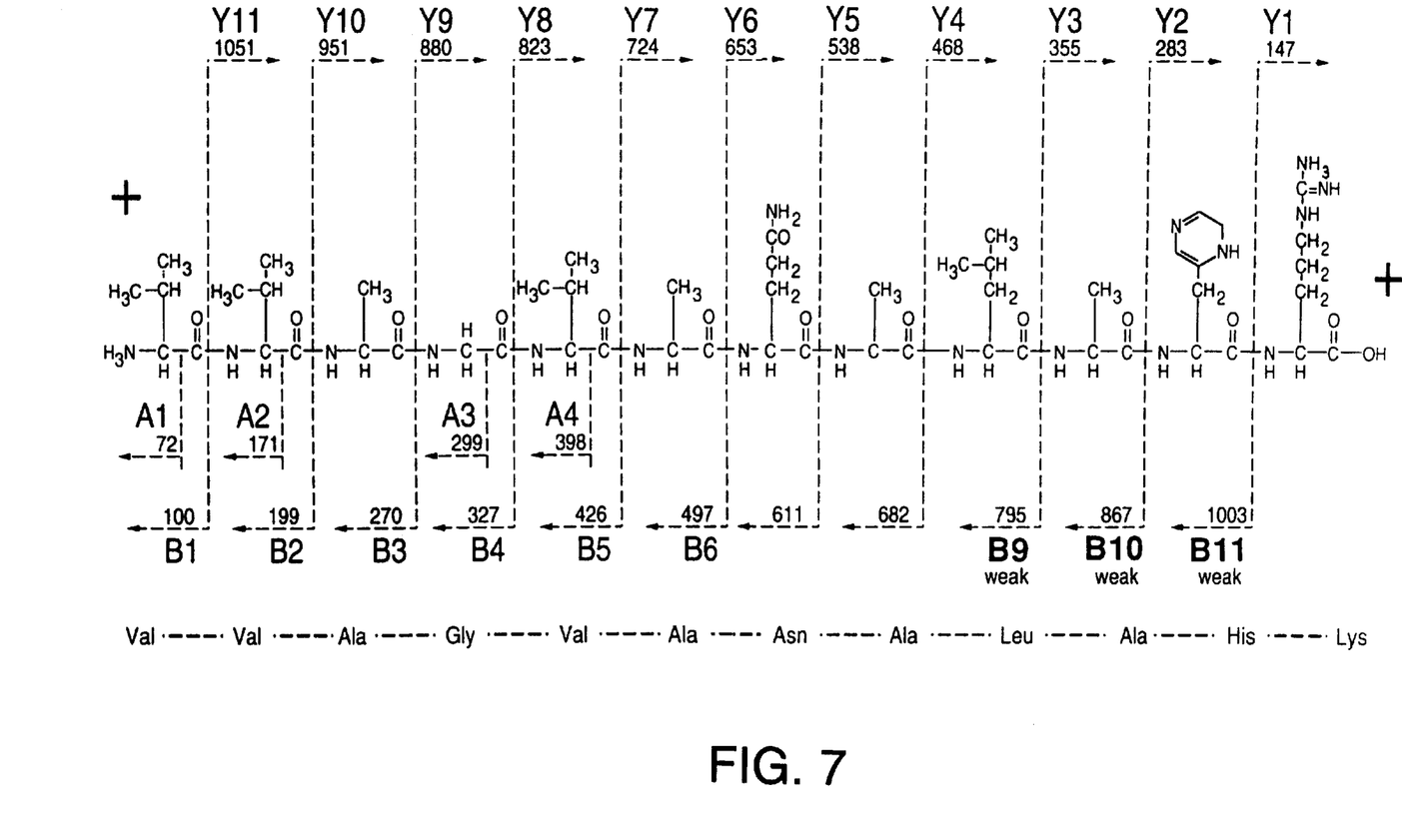
FIG. 7 shows the fragmentation pattern of tryptic fragment T-14 from the beta chain of human hemoglobin and demonstrates a method of analysis which may be used.
Figure 8:
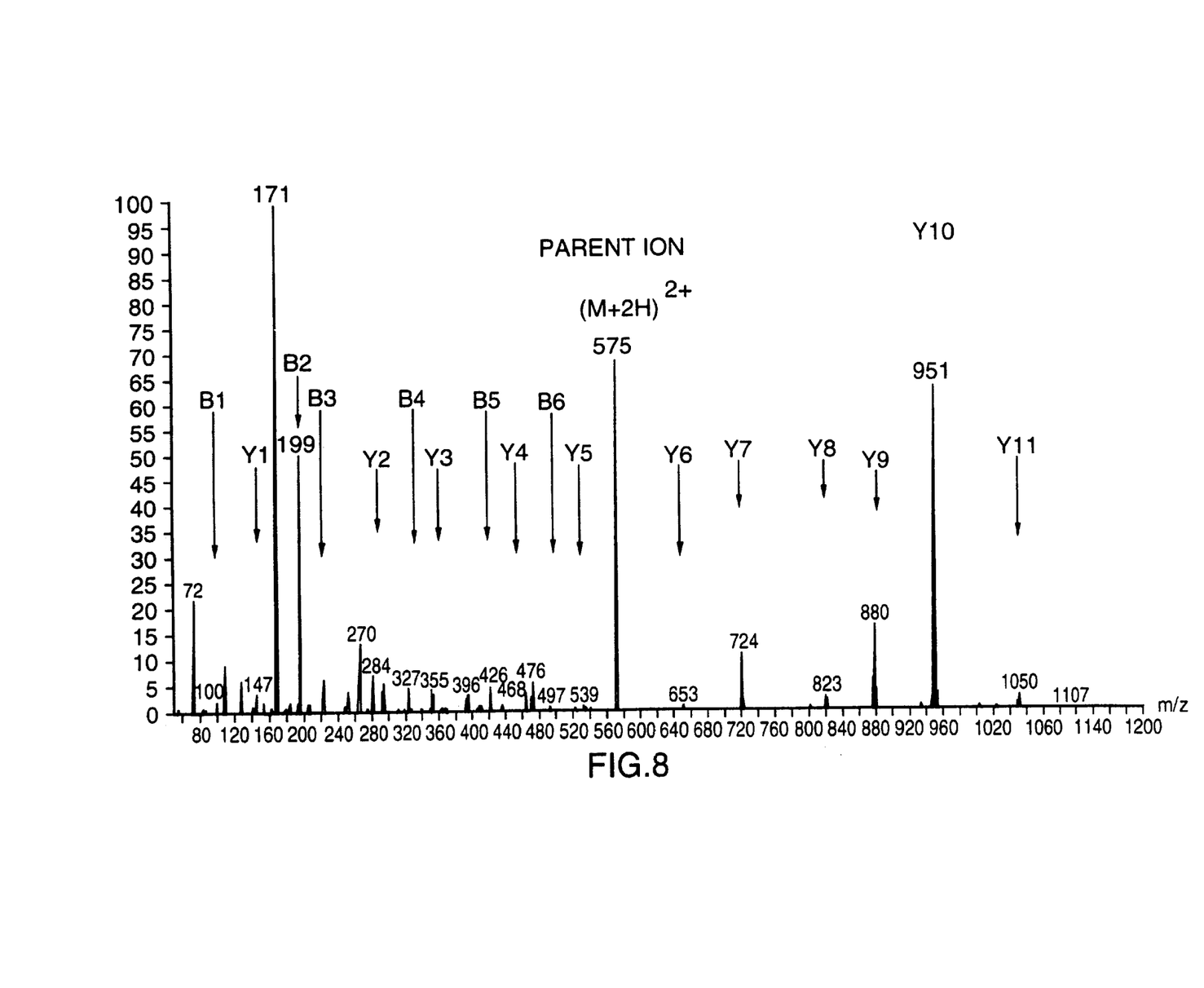
FIG. 8 shows a daughter ion mass spectrum of tryptic fragment T-14 from the beta chain of human hemoglobin and a method of analysis which may be used.

FIG. 8 shows a typical mass spectrum of daughter ions, obtained for mass 1148. A number of peaks are shown, representing daughter ions of various masses. Once the masses of the daughter ions have been determined, the sequence of the amino acids in the protein can be determined as indicated diagrammatically in FIG. 7. It will be recalled that each spectrum is composed of ion pairs, one ion constituting the left side of a cleavage and the other ion the right side of the cleavage, and that the sum of the masses of the ion pairs must equal the total mass of the tryptic fragment. The sequence of the amino acids in the molecule can thus be deduced from the family of ion pairs produced. The mass differences of the ion pairs correspond to the incremental mass (molecular weight minus $H_2O$) of the amino acid found in this position. For example, in FIG. 8, the difference between the masses of the ion pairs 823 and 724 is 99 which corresponds to the incremental mass of the amino acid valine (117−18=99) and therefore the amino acid valine is found in this position. The interpretation is shown diagrammatically in FIG. 7.

The key to the method is that virtually all of the tryptic fragment ions produced in the gas phase are doubly charged with one charge localized at each end of each ion. This double charging not only produces clean fragmentation with relatively easily interpretable sequence information, but also reduces the collision voltages required for the fragmentation of the tryptic fragments into daughter ions.

The collision voltage mentioned above is the DC bias voltage between orifice plate 50 (at the entrance to the vacuum chamber 26) and the centre quadrupole 32 where collision induced dissociation occurs. One reason why this collision voltage can now be low is because an ion with two charges travels with twice the kinetic energy of a singly charged ion under the influence of the same voltage potentials. Another reason why low collision voltages are needed is that the doubly charged ions are internally strained due to charge repulsion of the two protonated sites, and therefore fragmentation occurs relatively easily.

Typically, when argon is used as a collision gas, the collision voltage can be 20 to 30 volts. When nitrogen (which is lighter than argon) is used as a collision gas, about 25 to 35 volts are needed for fragmentation. When xenon (which is heavier than argon) is used as a collision gas, between 5 and 20 volts is typically suitable for fragmentation. This is far less than the kilovolt energies required for magnetic sector mass spectrometers.

Normally between 90 and 100 percent of the tryptic fragment ions in the gas phase are doubly charged when ion evaporation is used to convert them from the liquid to the gas phase. However there are three exceptions to the double charge rule. These are as follows.

Firstly, a carboxyl terminus tryptic fragment of the protein will not contain an arginine or a lysine and therefore will only be singly charged. Since this is far less frequent than the doubly charged fragments, therefore singly charged ions tend to identify the tryptic fragment of the carboxyl terminus.

Secondly, if there is an amino terminus which is carboxylated or blocked, it will only be singly charged. This is much rarer than the first exception listed above and can usually be ignored.

Thirdly, if the fragment contains an internal histidine, then a small percentage of the ions detected will be triply charged ions (the remainder will be doubly charged ions). This can be seen from FIG. 5, where peak 60 indicates doubly charged ions and peak 62 indicates triply charged ions. Again this represents an advantage, since the presence of triply charged ions thus indicates tryptic fragments containing a histidine.

This invention will be more fully understood by reference to the following examples.

EXAMPLE 1

Ion Evaporation Mass Spectrometer of Human Hemoglobin

A 5 mg/0.5 ml solution of human hemoglobin (Sigma #H-7379, 2× recrystallized and dialyzed by Sigma) was desalted with SEPHADEX G-25 columns in 1% acetic acid and then diluted. The resulting diluted solution was analyzed using ion evaporation mass spectrometer ( see pages 6 to 8 of the specification ) under the following conditions: continuous infusion at 3 µl/minute of human hemoglobin; concentration of 1 mg/ml, 16 µM or 16 pM µL (32 µMα and β chains) in 100% $H_2O$ in 0.5% formic acid. The ion evaporation mass spectrum of human hemoglobin is represented in FIG. 2. The known average molecular weight of hemoglobin is 61,988, and the known average molecular weight of the alpha and beta chains are 15,126.3 and 15,865.2, respectively. The molecular weight of the alpha chain was determined to be 15,126.6±1.3 and the molecular weight of the β chain was determined to be 15,864.9±1.4 from the spectrum.

EXAMPLE 2

Ion Evaporation Mass Spectrometry of Tryptic Fragments

A sample of human hemoglobin (Sigma #H-7379, 2× recrystallized and dialysed by Sigma) was desalted with SEPHADEX G-25 columns in 1% acetic acid, diluted, digested with trypsin using the procedure described for BSA by E. R. Hoff in LC.GC Vol. 7(4)-p. 320 (1989), and fractionated by HPLC (1 mm×10 cm C8 column gradient 5% $CH_3CN$/0.1% trifluoroacetic acid). Ion evaporation mass spectrometry (50 µl/min, 5 µl injected) of the fraction was carried out using the procedure as disclosed on pages 6 to 8 of the specification and the resulting spectrum is represented in FIG. 3. FIG. 3 shows the total ion current trace of the tryptic digest of the human hemoglobin sample. The ion evaporation mass spectrum at scan numbers 111, 158, 177 and 100 are represented in FIGS. 4A, 4B, 4C and 5, respectively. The spectra indicates the molecular weights of the tryptic fragments present (1214, 1070, 2058 and 1148).

It is noted that there is a satellite peak (for example at a mass to charge ratio (m/z) of 678 in FIG. 4A) which represents acetonitrile, the solvent used in the HPLC. It would have been expected that this satellite peak would be located 41 m/z (which corresponds to the molecular weight of acetonitrile) from the m/z of the peptides. However, the satellite peak is spaced at approximately 20 m/z from the m/z of the peptides indicating that a significantly high percentage (at least 90%) of the peptides are doubly charged.

Figure 5:
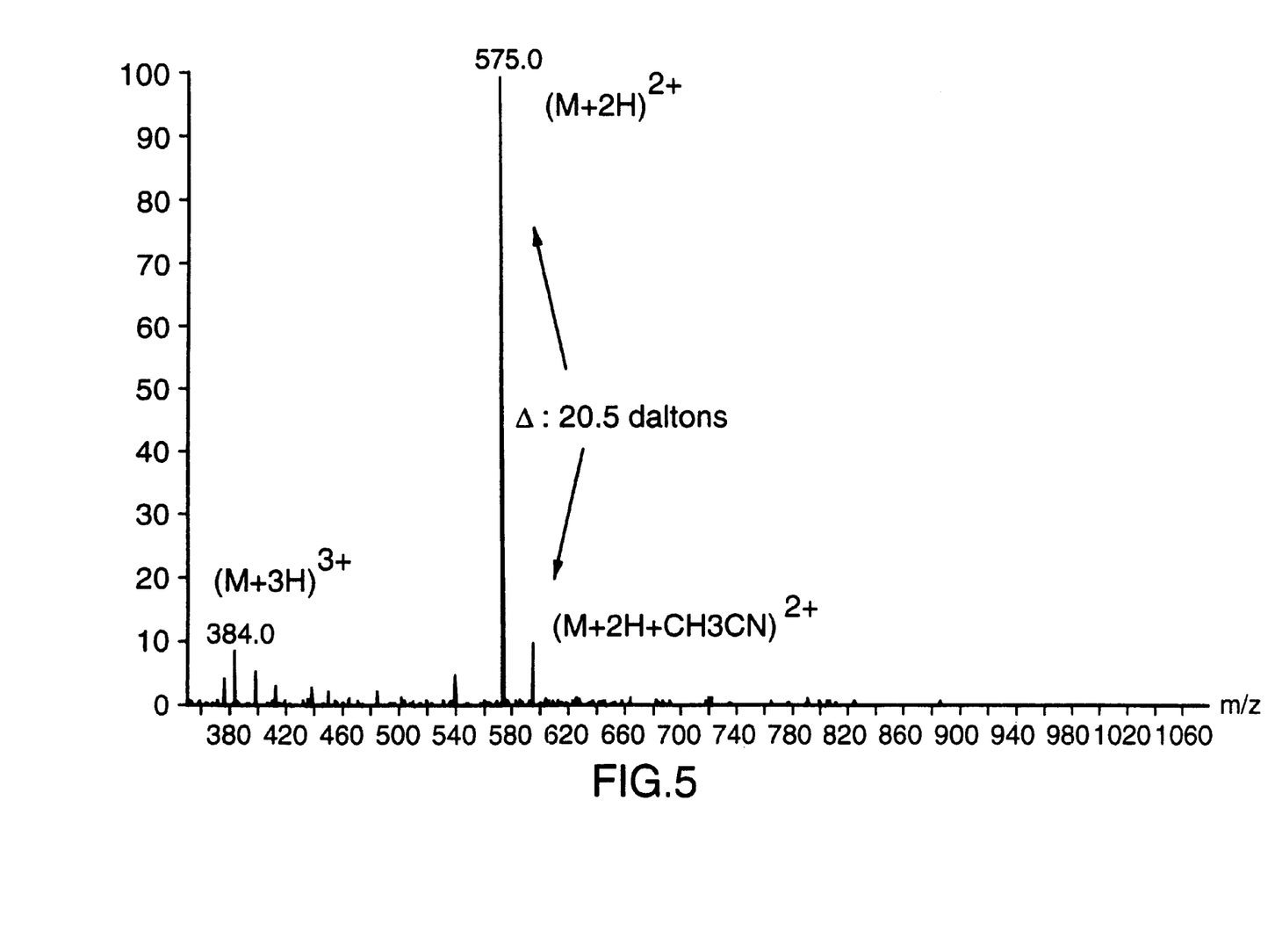
FIG. 5 shows the mass spectrum for scan 100 from the tryptic digest of FIG. 3.

It is also noted with respect to FIG. 5, that there is a tryptic fragment having a triple charge at m/z 384 indicating that histidine is present in the tryptic fragment.

EXAMPLE 3

Determination of the Molecular Weight of the Peptide Represented by Scan No. 100

The $(M+2H)^{2+}$ ions of the fraction corresponding to Scan No. 100 (see example 2) were subjected to collision induced dissociation with argon using 20–30 volts and the resulting daughter ions were analyzed in an ion evaporation mass spectrometer (see page 10 of the specification). FIG. 8 represents the daughter ion spectrum of the $(M+2H)^{2+}$ ion of m/z 575 in FIG. 5. The sequence of the peptide is deduced from the mass differences of ion pairs, which correspond to the incremental mass (molecular weight minus $H_2O$) of one of the amino acids occurring in proteins. For example, in FIG. 8 the difference between the masses of the ion pairs 724 and 653 is 71, which corresponds to the incremental mass of the amino acid alanine (the molecular weight of alanine 89 minus 18). Similarly, the difference between the masses of the ion pairs 823 and 724 is 99 indicating that the amino acid valine (the molecular weight of valine 117 minus 18) is at this position. This is shown diagramatically in FIG. 7.

We claim:

1. A method for determining the sequence of a test peptide or a test polypeptide comprising:
    (A) cleaving the amide backbone of the test peptide or the test polypeptide by treatment with Trypsin to form a sub-population of fragments having carboxy-terminal lysine or arginine residues;
    (B) ionizing said fragments to produce doubly charged gas phase ions;
    (C) further fragmenting the gas phase ions under conditions which produce a population of daughter ions of incremental molecular weight, which population of daughter ions results substantially from fragmentation of the amide backbone of said fragments;
    (D) determining the molecular weight of said gas phase ions and daughter ions by mass spectrometry; and
    (E) determining the sequence of at least a portion of the test peptide or the test polypeptide from the determined molecular weights.

2. The method of claim 1, further comprising separating said fragments of the test peptide or test polypeptide prior to ionizing said fragments to produce gas phase ions.

3. The method of claim 2, wherein said fragments of the test peptide or test polypeptide are separated based on size, solubility, electric charge and/or ligand specificity prior to ionization.

4. The method of claim 3, wherein said fragments are separated using one or more procedures selected from the group consisting of gel-filtration, isoelectric precipitation, electrophoresis, isoelectric focusing, ion exchange chromatography, and affinity chromatography.

5. The method of claim 3, wherein said fragments are separated using high performance liquid chromatography.

6. The method of claim 3, wherein said fragments are separated using capillary zone electrophoresis.

7. The method of claim 3, wherein said fragments are separated using isotachophoresis.

8. The method of claim 5 or 1, wherein said test peptide or test polypeptide or said fragments thereof are treated with an agent to reduce disulfide bonds before ionizing said test peptide or test polypeptide, or said fragments thereof.

9. The method of claim 1 or 2, wherein the step of fragmenting the gas phase ions under conditions which produce a population of daughter ions utilizes collision-induced dissociation with a collision voltage of less than one kilovolt.

10. The method of claim 1 or 2, wherein said gas phase ions are produced by ion evaporation ionization.

11. The method of claim 10, wherein the molecular weight of said gas phase ions and daughter ions are determined by ion spray mass spectrometry.

12. The method of claim 11, wherein at least 90% of the gas phase ions are doubly charged.

13. The method of claim 1, wherein at least 90% of the gas phase ions are doubly charged.

14. A method of analyzing a test peptide or a test polypeptide comprising:
    (A) generating fragments of the test peptide or the test polypeptide by treatment with Trypsin to produce a population of fragments having carboxy-terminal lysine or arginine residues;
    (B) ionizing said fragments to produce doubly charged gas phase ions under conditions which produce a population of daughter ions of incremental molecular weight;
    (C) determining the molecular weight of said gas phase ions and daughter ions by ion spray mass spectrometry.

15. The method of claim 14, further comprising separating said fragments of the test peptide or test polypeptide prior to ionizing said fragments to produce gas phase ions.

16. A method for interpreting the mass spectrum of a test peptide or a test polypeptide comprising:
    (A) providing a population of Tryptic fragments of the test peptide or the test polypeptide having carboxy-terminal lysine or arginine residues and ionizing said fragments to produce doubly charged gas phase ions;
    (B) obtaining the mass spectra, and calculating molecular weights there from, for the fragments and for a population of daughter ions of incremental molecular weight, which population of daughter ions results substantially from fragmentation of the amide backbone of said fragments; and
    (C) determining at least a portion of the sequence of the test peptide or the test polypeptide by comparing differences in molecular weights between said gas phase ions and daughter ions to the molecular weight of amino acids.

17. A method for determining the sequence of a test peptide or a test polypeptide comprising:
    (A) cleaving the amide backbone of the test peptide or the test polypeptide by treatment with Trypsin to form a sub-population of fragments having carboxy-terminal lysine or arginine residues;
    (B) ionizing, by ion evaporation ionization, said fragments to produce doubly charged gas phase ions;
    (C) further fragmenting the gas phase ions under conditions which produce a population of daughter ions of incremental molecular weight utilizes collision-induced dissociation with a collision voltage of less than one kilovolt, which population of daughter ions results substantially from fragmentation of the amide backbone of said fragments;
    (D) determining the molecular weight of said gas phase ions and daughter ions by mass spectrometry; and,
    (E) determining the sequence of at least a portion of the test peptide or the test polypeptide from the determined molecular weights.

18. The method of claim 17, further comprising separating said fragments of the test peptide or test polypeptide prior to ionizing said fragments to produce gas phase ions.

19. The method of claim 18, wherein said fragments of the test peptide or test polypeptide are separated based on size, solubility, electric charge and/or ligand specificity prior to ionization.

20. The method of claim 19, wherein said fragments are separated using one or more procedures selected from the group consisting of gel-filtration, isoelectric precipitation, electrophoresis, isoelectric focusing, ion exchange chromatography, and affinity chromatography.

21. The method of claim 19, wherein said framents are separated using high performance liquid chromatography.

22. The method of claim 19, wherein said fragments are separated using capillary zone electrophoresis.

23. The method of claim 19, wherein said fragments are separated using isotachophoresis.

24. The method of claim 17 or 19, wherein said test peptide or test polypeptide or said fragments thereof are treated with an agent to reduce disulfide bonds before ionizing said test peptide or test polypeptide, or said fragments thereof.

25. The method of claim 17 or 19, wherein the molecular weight of said gas phase ions and daughter ions are determined by ion spray mass spectrometry.

26. The method of claim 25, wherein at least 90% of the gas phase ions are doubly charged.

27. The method of claim 17, wherein at least 90% of the gas phase ions are doubly charged.

* * * * *